US00PP08566P

United States Patent [19]

Bennett, deceased et al.

[11] Patent Number: Plant 8,566

[45] Date of Patent: Feb. 1, 1994

[54] CUDDLE UP

[76] Inventors: Cecilia L. D. Bennett, deceased, late of Chula Vista; by Susan M. O'Brien, Administrator, 489 Minot Ave., Chula Vista, both of Calif. 91910

[21] Appl. No.: 812,683

[22] Filed: Dec. 23, 1991

[51] Int. Cl.[5] ..... A01H 5/00

[52] U.S. Cl. ..... Plt./7.1

[58] Field of Search ..... Plt. 7.1, 8.2, 9, 11, Plt. 18, 22, 26

*Primary Examiner*—Howard J. Locker

*Assistant Examiner*—E. F. McElwain

[57] ABSTRACT

The subject of the present disclosure is a new and distinct variety of miniature rose plant, named 'Cuddle Up', which is characterized by blooms of pale yellow (ranging from near Mimosa Yellow to near Empire Yellow) with a pink blush (ranging from near Carmine Rose to near Neyron Rose which fades to near Orient Pink to near Shell Pink as the bloom opens). Blooms of this rose are usually borne one to a stem with hybrid tea form but on occasion may be produced in sprays of 3 to 5 or more. The bush is vigorous, well-branched and produces moderate to heavy quantity of blooms.

1 Drawing Sheet

The present invention relates to a new and distinct variety of a hardy, dwarf, bush plant of the miniature class; the variety being primarily characterized as yellow blend.

The variety is further characterized by:

Long stemmed blooms of hybrid tea-type form, borne usually one to a stem but on occasion in sprays of 3 to 5 or more. The blooms are held very erect and well above the foliage.

The plant ranges in height from 18 to 24 inches (45 to 60 cm). The canes are sturdy and erect with moderate branching and medium to heavy foliage covering. The plant is a moderate to heavy bloomer that does well either in the greenhouse or outdoors.

The plant has good growth habits, is well-shaped and attractive, bearing numerous leaflets of average size. Asexual reproduction of the new variety by cuttings derived from the plant stem, as performed at Chula Vista, Calif., shows that the foregoing characteristics and distinctions come true to form and are established and transmitted through succeeding propagations.

The seed parent was Lagerfeld (U.S. Plant Pat. No. 6,812), and the pollen parent was My Delight (U.S. Plant Pat. No. 5,437). It differs from its seed parent in the following ways. It is a miniature rose of yellow blend class, and Lagerfeld is a grandiflora of the mauve class. It differs from from pollen parent in the following ways. It produces flowers of pale yellow with a pink blush on a large plant, and My Delight produces blooms in light pink on compact plant.

The single color photographic view shows, in plan view, a bouquet of 'Cuddle Up' in various stages of maturity from bud stage to nearly open bloom stage.

The descriptive matter which follows pertains to roses grown and color values observed in plants and nearly opened blooms in the months of March through November 1991. The plants were grown outdoors in Chula Vista, Calif., and are believed to be accurate standards for this cultivar in similar conditions of soil and climate elsewhere.

Referring now specifically to the new and distinct variety of miniature rose plant named Cuddle Up', the following is a detailed description thereof in outline; all major color plate identifications being by reference to The British Colour Council Horticultural Chart, except where common terms of color definition are employed.

Type: Hardy, drawf, bushy, greenhouse or outdoor, exhibition or garden decorative potted plant.

Class: Miniature.

Variety name: Cuddle Up.

Flowers borne: Usually one to a stem, but occasionally in sprays of 3 to 5 or more on erect stems with foliage well below the blooms.

Quantity of bloom: Moderate to heavy both outdoors or greenhouse grown.

Bud:

*Peduncle.*—Average length (30 to 50 mm); average diameter and sturdy; ranging from near Scheeles Green (860/3 to 860/1 page 176) with occasional tinting of bronze.

*Hairs.*—Extremely small and sparse with a reddish color; located over the surface of the peduncle and calyx tube.

*Calyx.*—Color range same as peduncle.

*Opening.*—Opens well in all weather.

Bloom:

*Size when fully open.*—Average for a miniature variety (40 to 50 mm).

*Petalage.*—Double — 25 to 30 petals, arranged regularly, plus 5 to 10 petaloids.

*Form.*'Urn-shaped to ovoid as the bloom opens. The petals remain somewhat cupped with the apex and/or margins reflexed outward, becoming at maturity more loosely cupped.

Petals: Fairly thick with good substance; both the upper and under surfaces of all petals have a matte finish.

*Shape.*—Outer petals are of a broad obovate form. The intermediate petals are very much like the outer petals only narrower. The inner petals are a broad lanceolate form; and the petaloids are also lanceolate with some occasional irregularities.

Color: Newly opened flowers from plants grown outdoors (March through November of 1991), Chula Vista, Calif.

*All petals.*—Upper surfaces — Ranging from near Mimosa Yellow (602/1 to 602/3 page 143) to near Empire Yellow (603/1 to 603/3 page 66) with a blush on all petal margins of near Carmine Rose (621/1 to 621/3 page 75) to near Neyron Rose (623/1 to 623/3 page 76). The blush will fade to ranges of near Orient Pink (416 to 416/3 page 124) to near Shell Pink (516/1 to 516/3 page 135) as the blooms open. In the fully open bloom, there is little or no evidence of the pink blush; and the yellow tones are paler as well. Under surfaces — Slightly lighter tones of upper surfaces.

*General color effect.*—Newly opened flowers — Pale yellow with a blush of pink on all margins. Three days open — Slight fading of blush on petal margins only. Three to five days open — Continued fading of blush on margins and yellow tones as well.

*Flower longevity.*—(March through November 1991). Plant in pot 5 to 7 days from bud with sepals reflexed to fully open bloom. Holding at fully opened for 5 to 7 days longer. Cut bloom at living room temperature 10 to 14 days or longer.

Reproductive organs:

*Stamens.*—A generous amount arranged uniformly around the pistil.

*Filaments.*—Varying in length with shorter filaments more proximal to the pistil; pale yellow in color with anthers of golden yellow.

*Pollen.*—Abundant.

*Pistil.*—Short, spreading and abundant; pale yellow to reddish at the cap.

*Ovaries.*—All encased in calyx.

*Hips.*—Some.

*Seeds.*—3 to 5 or more in each hip.

Foliage:

*Sepals.*—Permanent; spear-shaped; simple and glabrous open as the bloom opens, recurving against the peduncle, when the bloom is fully opened.

*Leaves.*—5 to 7 leaflets on average; medium size for a miniature rose plant.

*Leaflets.*—Broad ovate-shaped.

*Margins.*—Very serrated with tinting of bronze, especially noticeable on the newer foliage.

*Color.*—Ranging from near Spinach Green (0960/3 to 0960 page 187) to near Schleeles Green (860/1 to 860 page 175) with occasional bronzing of the margins, especially on the newer foliage. Upper surfaces have a semi-glossy finish, and the under surfaces have a matte finish of a slightly ligher shade than the upper surfaces.

*Rachis.*—Medium strength; upper surface is grooved with very small hairs over the length of it. Under surface has few if any hairs but does contain 2 to 5 small thorns.

*Stipules.*—Varying in length from small to medium; average width; tapering auricles angled outward at about 45 degrees.

Growth:

*Habit.*—Dwarf, bush; above average for a miniature rose plant.

*Growth.*—Vigorous and well-branched.

*Canes.*—Medium diameter; sturdy; held erect.

*Main stems.*—Color range same as foliage.

*Thorns.*—Averaging less than 5 to 10 per 10 cm on the main stems and branches. Reddish in color; average size; slender and hooked slightly downward.

*Branches.*—Color range same as foliage.

The miniature rose plant and its flowers as herein described may vary in slight detail due to climate, soil and cultural conditions under which the variety may be grown; the present description being of the variety as grown in Chula Vista, Calif.

The following is claimed:

1. A new and distinct variety of miniature rose plant, named 'Cuddle Up', of hardy, dwarf, vigorous growth, well-branched and attractive in appearance, substantially as illustrated and described, characterized by its hybrid tea form blooms of ranging from near Mimosa Yellow to near Empire Yellow with a pink blush ranging from near Carmine Rose to near Neyron Rose that fades to tones ranging from near Orient Pink to near Shell Pink; the blooms are usually borne one to a stem but occasionally in sprays of 3 to 5 or more.

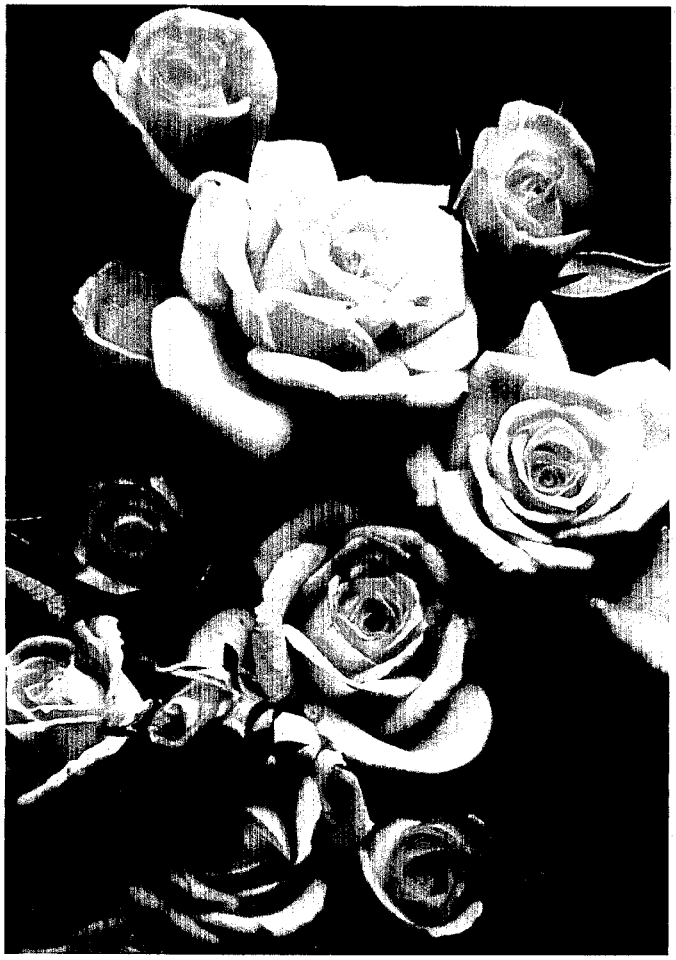

* * * * *